(12) United States Patent
Chen et al.

(10) Patent No.: US 10,145,178 B2
(45) Date of Patent: Dec. 4, 2018

(54) ROLLER CONE SEAL FAILURE DETECTION USING AN INTEGRATED COMPUTATIONAL ELEMENT

(71) Applicant: Halliburton Energy Services, Inc., Houston, TX (US)

(72) Inventors: Shilin Chen, Montgomery, TX (US); Micheal Burl Crawford, Montgomery, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 202 days.

(21) Appl. No.: 14/787,423

(22) PCT Filed: May 22, 2013

(86) PCT No.: PCT/US2013/042270
§ 371 (c)(1),
(2) Date: Oct. 27, 2015

(87) PCT Pub. No.: WO2014/189508
PCT Pub. Date: Nov. 27, 2014

(65) Prior Publication Data
US 2016/0115740 A1   Apr. 28, 2016

(51) Int. Cl.
| E21B 10/24 | (2006.01) |
| E21B 10/25 | (2006.01) |
| E21B 12/00 | (2006.01) |
| G01N 21/31 | (2006.01) |
| G01N 33/26 | (2006.01) |
| E21B 10/22 | (2006.01) |

(52) U.S. Cl.
CPC .............. *E21B 10/24* (2013.01); *E21B 10/25* (2013.01); *E21B 12/00* (2013.01); *G01N 21/31* (2013.01); *G01N 33/26* (2013.01); *E21B 2010/225* (2013.01)

(58) Field of Classification Search
CPC .......... E21B 10/24; E21B 12/02; E21B 10/08; E21B 10/25; E21B 12/00; E21B 2010/225; G01N 21/31; G01N 33/26; G02B 6/29361
See application file for complete search history.

(56) References Cited

U.S. PATENT DOCUMENTS

| 5,475,309 | A |    | 12/1995 | Hong et al. |
| 5,739,916 | A | *  | 4/1998  | Englehaupt ............ G01N 21/31 356/414 |
| 6,198,531 | B1 | * | 3/2001  | Myrick ...................... G01J 3/28 356/213 |
| 6,230,822 | B1 |   | 5/2001  | Sullivan et al. |

(Continued)

OTHER PUBLICATIONS

International Search Report and Written Opinion, dated Feb. 21, 2014, 14 pages; Korean International Searching Authority.

*Primary Examiner* — Daniel P Stephenson

(57) ABSTRACT

A method and apparatus for determining the effectiveness of bearing seals in a roller cone drill bit. The bit includes a sensor in optical communication with the bearing lubricant. The sensor includes a light source, an optical filter, and an optical detector arranged so that light interacts with the lubricant, is filtered, and detected, wherein the detected light is indicative of the amount of contaminant within the lubricant. The optical filter is preferably an integrated computing element that filters preselected orthogonal components from the light.

16 Claims, 2 Drawing Sheets

(56) References Cited

U.S. PATENT DOCUMENTS

| | | | |
|---|---|---|---|
| 6,466,513 B1 | 10/2002 | Pabon et al. | |
| 6,529,276 B1 * | 3/2003 | Myrick | G01J 3/02 |
| | | | 356/310 |
| 7,697,141 B2 * | 4/2010 | Jones | E21B 47/102 |
| | | | 356/445 |
| 8,049,881 B2 * | 11/2011 | Myrick | A61K 8/046 |
| | | | 356/300 |
| 8,624,191 B2 * | 1/2014 | Franke | F16C 19/52 |
| | | | 250/338.1 |
| 2003/0062197 A1 | 4/2003 | Moran et al. | |
| 2010/0157304 A1 * | 6/2010 | Takahashi | F16C 19/52 |
| | | | 356/442 |
| 2011/0215234 A1 | 9/2011 | Rose | |
| 2014/0172177 A1 * | 6/2014 | Jamison | G01V 8/02 |
| | | | 700/281 |
| 2016/0115740 A1 * | 4/2016 | Chen | E21B 10/25 |
| | | | 175/40 |
| 2017/0205338 A1 * | 7/2017 | Coates | G01N 21/31 |

* cited by examiner

ROLLER CONE SEAL FAILURE DETECTION USING AN INTEGRATED COMPUTATIONAL ELEMENT

CROSS REFERENCE TO RELATED APPLICATIONS

The present application is a U.S. National Stage patent application of International Patent Application No. PCT/US2013/042270, filed on 22 May 2013, the benefit of which is claimed and the disclosure of which is incorporated herein by reference in its entirety.

FIELD

The present disclosure relates generally to drill bits for boring holes in the earth, and specifically to lubrication systems for roller cone bits.

BACKGROUND

Roller cone bit used in the oil and gas drilling industry typically have sealed ball bearings that are lubricated from a lubricating system. Grease is often used as the lubricant. Of the bearing components, the bearing seal typically has the lowest mean time between failure, so that the bearing seal effectiveness typically determines the life of the bearing system. As the seal wears, the grease may become contaminated with drilling mud and water, which are gradually introduced into the lubrication system. Accordingly, the amount of contaminant fluid within the lubricant indicates the effectiveness of the seal, and when the contaminant reaches a predetermined limit, continued drilling must cease, lest a bearing failure occur that can leave one or more roller cones at the bottom of the borehole and require a costly fishing operating to retrieve them.

Prior art techniques are known for sensing an impending bearing failure due to a bearing seal failure. In some cases, bearing seal failure is gradual, but in other cases, bearing failure may occur catastrophically with little to no warning. Prior art methods of detecting seal failure may not be sensitive enough predict an imminent seal failure or responsive enough detect a seal failure and rapidly communicate such condition before significant bearing damage occurs. Accordingly, it is desirable to detect seal failure of a roller cone bit in real time.

BRIEF DESCRIPTION OF THE DRAWINGS

Embodiments are described in detail hereinafter with reference to the accompanying figures, in which.

DETAILED DESCRIPTION

Figure 1:
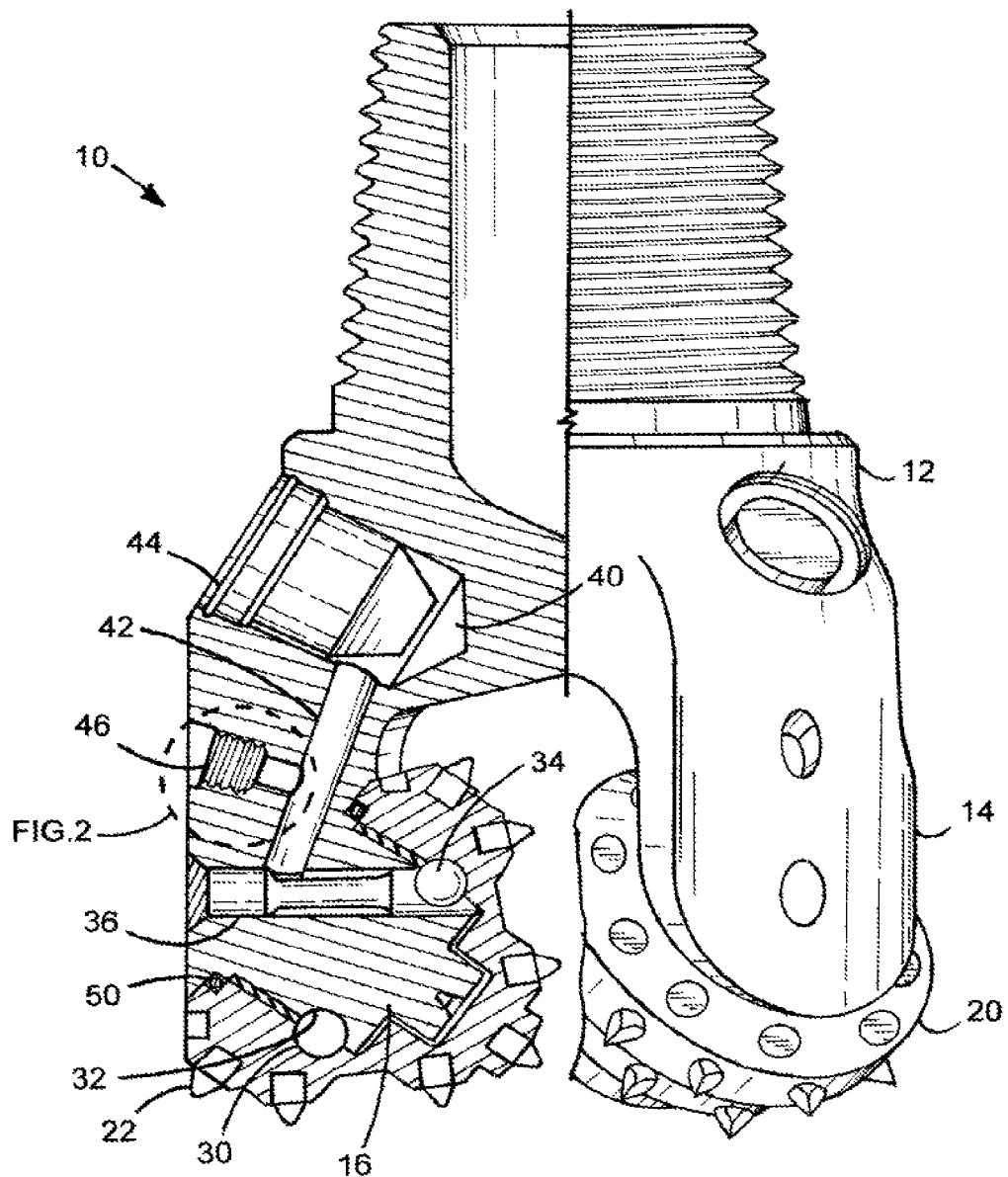
FIG. 1 is an elevation view with one-quarter cut away to reveal a longitudinal cross section of a roller cone drill bit according to a present embodiment, showing a bit body having arms terminating in journals, cutter assemblies rotatively mounted to the journals with ball bearings, and an internal bearing lubrication system.
Figure 2:
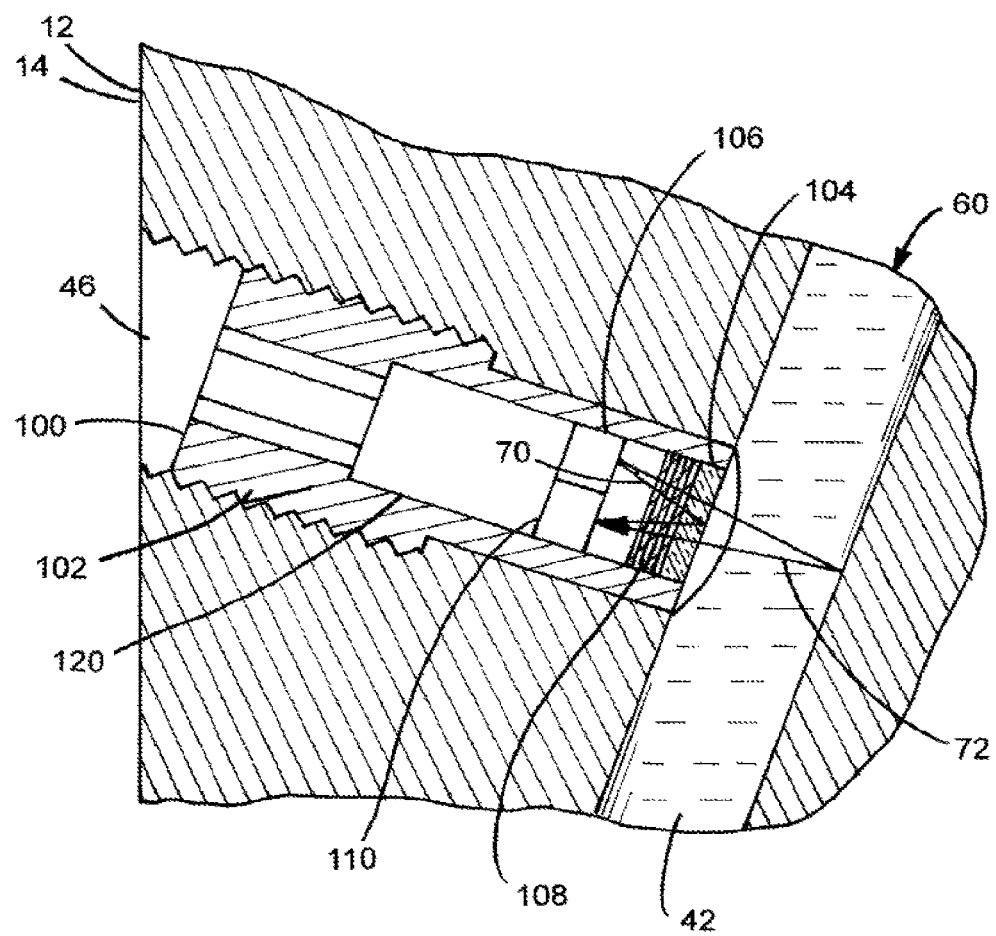
FIG. 2 is an enlarged longitudinal cross section of an optical sensor according to a present embodiment for use within the lubrication system of the drill bit of FIG. 1, showing a light source, an optical filter and an optical detector located within a cylindrical housing with a transparent window located at one end for immersion in a lubricant.

FIG. 1 illustrates a roller cone drill bit 10 that is arranged for including an optical sensor 100, as shown in FIG. 2, which is specifically designed and configured for detecting the presence of water within a grease, lubricant, or other fluid. Bit 10 includes a bit body 12, which preferably includes arms 14 that terminate as journals 16. A cutter assembly 20, typically a roller cone carrying a large number discrete cutters 22, is rotatively captured on each journal 16.

In one embodiment, the interior circumference of cutter assembly 20 has a semi-circular groove 30 formed therein that defines an outer bearing race. Likewise, the outer circumference of journal 16 has a semicircular groove formed therein that defines an inner bearing race 32. A plurality of hardened ball bearings 34 are received in the circular cavity defined between the inner and outer races 30, 32 to rotatively capture cutter assembly 20 upon journal 16. A ball passageway 36, which is plugged during ordinary use, is formed between the exterior surface and the circular bearing cavity within each arm 14 to allow the ball bearings to be loaded and unloaded as needed for installation, maintenance, and repair.

One or more cavities are formed in bit body 12 to serve as a reservoir 40 for lubricant. Reservoir 40 is in fluid communication with the ball bearings 34 and bearing races 30, 32, ideally through a conduit 42 that connects ball passageway 36 to reservoir 40. A diaphragm, piston, or similar pressure regulation assembly 44 may be provided to pressurize the lubrication system to minimize ingress of contaminants into the bearing assembly. To that end, one or more journal/cutter assembly seals 50 are provided to keep lubricant in and contaminants out of the bearing assemblies.

A seal failure sensor or monitor 100 (FIG. 2) is positioned to be in fluid communication with the lubricant. In one embodiment, the sensor is positioned in a socket 46 that is fluidly coupled to conduit 42. However, in other embodiments, the sensor may be positioned elsewhere in the drill bit about the lubricant system. Sensor 100 may be unitary, or it may consist of several discrete parts.

FIG. 2 is a detailed view of socket 46 of drill bit 10 of FIG. 1, showing sensor 100 positioned therein according to one embodiment. Sensor 100 includes a housing 102, which may be cylindrical and threaded into socket 46. However, other techniques to mount sensor 100 within bit 10 may be used as appropriate.

The inner end of housing 102 includes, or is formed by, a window 104, which preferably forms a fluid tight seal with housing 102 but is transparent to wavelengths of light of interest to the optical sensor 100. Window 104 is in optical communication, and ideally in physical contact, with lubricant 60, which may be contained in conduit 42 as shown in FIG. 2. Sensor 100 includes a light source 106, and optical filter 108, and an optical detector 110, which are all preferably but not necessarily positioned within housing 102. The light source 106, and optical filter 108, and an optical detector 110 may all be discrete components, or two or more may be conjoined. Regardless, these components are positioned so that light from light source 106 interacts with lubricant, passes through optical filter 108 (either before or after interaction with lubricant 60, as appropriate), and is received at optical detector 110.

As illustrated by arrows, light interaction with lubricant 60 may be by reflection (predominantly at the window/lubricant interface) as shown by arrow 70, by transmission (with reflection off of the conduit wall), as shown by arrow 72, or by a combination of these mechanisms. Indeed, the light from light source 106 may also be subject to refraction, diffusion, and absorption so as long as some of the interacted light reaches optical detector 110.

Sensor 100 may also contain a processing and telemetry module 120 that is operatively coupled to optical detector 110 for processing signals from optical detector 110 and communicating them to a remote location, for example, the surface of the earth. In this manner, drilling operators can be accurately advised in real time of the amount of water ingress in the bit lubrication system and accordingly, the effectiveness of the seals. Various forms of telemetry may be used, including electric, electromagnetic, acoustic, etc. As such telemetry techniques are well known in the art, further detail regarding telemetry is not provided herein.

In a first embodiment, each cutter assembly 20 may have an individual, dedicated optical sensor 100, which is preferably located within each arm 14. Telemetry may include signals from each sensor, which may be continual or sequential, for example. Alternatively, bit 100 may include a single optical detector 100, which monitors a common lubrication system that serves all of the cutter assemblies 20 on the bit.

The principle of operation of sensor 100 is now described: When light interacts with matter, for example via transmission or reflection, it carries away information about the physical and chemical properties of the matter with which it interacted. A property of the light, for example its intensity, may be measured and interpreted to provide information about the matter with which it interacted. That is, the data carried by the light through its intensity may be measured to derive information about the matter.

In general, it is difficult to convert a simple measurement of light intensity into information because of interfering data. That is, several factors may contribute to the intensity of light, even in a relatively restricted wavelength range. It is often impossible to adequately measure the data relating to one of these factors, because the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. In particular, a lubricant sample may be illuminated so that light from the lubricant carries information such as the sample's water content. Light from each of several samples may be directed to a series of bandpass filters which separate predetermined wavelength bands from the light. Light detectors following the bandpass filters measure the intensity of each light band. If the water content of each lubricant sample is measured using conventional means, a multiple linear regression of several measured bandpass intensities against the measured water content for each sample may produce an equation such as:

$$y = a_0 + a_1 w_1 + a_2 w_2 + \ldots + a_n w_n \quad \text{(Equation 1)}$$

where y is water content, $a_n$ is a constant determined by the regression analysis, and $w_n$ is the light intensity for each wavelength band.

Equation 1 may be used to estimate water content of subsequent samples of the same lubricant type. Depending on the circumstances, however, the estimate may be unacceptably inaccurate, because factors other than water may affect the intensity of the wavelength bands. Moreover, these other factors may not change from one sample to the next in a manner consistent with water.

A more accurate estimate may be obtained by compressing the data carried by the light into principal components. To obtain the principal components, spectroscopic data is collected for a variety of samples of the same type of light, for example from illuminated samples of the same type of lubricant. The light samples are spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which is generally well known by routineers in this art apart from the particular teachings of the present disclosure.

Briefly, principal component analysis is a dimension reduction technique which takes m spectra with n independent variables and constructs a new set of eigenvectors that are linear combinations of the original variables. The eigenvectors may be considered a new set of plotting axes. The primary axis, termed the first principal component, is the vector which describes most of the data variability. Subsequent principal components describe successively less sample variability, until only noise is described by the higher order principal components.

Typically, the principal components are determined as normalized vectors. Thus, each component of a light sample may be expressed as $x_n \hat{z}_n$, where $x_n$ is a scalar multiplier and $\hat{z}_n$ is the normalized component vector for the $n^{th}$ component. That is, $\hat{z}_n$ is a vector in a multi-dimensional space where each wavelength is a dimension. Normalization determines values for a component at each wavelength so that the component maintains its shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 \hat{z}_1 + x_2 \hat{z}_2 + \ldots + x_n \hat{z}_n$$

The scalar multipliers $x_n$ may be considered the "magnitudes" of the principal components in a given light sample when the principal components have a standardized magnitude as provided by normalization.

Because the principal components are orthogonal, they may be used in a relatively straightforward mathematical procedure to decompose a light sample into the component magnitudes which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

Thus, the principal components of light may be used to accurately estimate information carried by the light. Accordingly, light that has interacted with a test sample of a known material contaminated with an unknown quantity of a known contaminant can be resolved into its principal components and compared to previously-measured principal components of reference samples with known quantities of contaminants to determine the quantity of contaminant within the test sample. This is the operating principle of the present embodiment.

In a preferred embodiment, optical filter 104 is a multivariate optical element, also known as an Integrated Computing Element ("ICE"), which is specifically designed and structured to detect the amount of water or other contaminant in grease or other lubricant. The design and operation of ICE structures are described in, for example, U.S. Pat. Nos. 6,198,531; 6,529,276; 7,697,141; and 8,049,881, each being owned by the Assignee of the present disclosure, Halliburton Energy Services, Inc., of Houston, Tex.

The Abstract of the disclosure is solely for providing the United States Patent and Trademark Office and the public at large with a way by which to determine quickly from a cursory reading the nature and gist of technical disclosure, and it represents solely one or more embodiments.

While various embodiments have been illustrated in detail, the disclosure is not limited to the embodiments shown. Modifications and adaptations of the above embodiments may occur to those skilled in the art. Such modifications and adaptations are in the spirit and scope of the disclosure.

What is claimed:

1. A unitary sensor for measuring a concentration of water within a fluid, comprising:
   a housing;
   a window formed in an inner end of said housing, and forming a fluid tight seal with said housing;
   an optical filter sealed in said housing;
   an optical detector sealed in said housing so as to receive light through said sensor; wherein said optical filter and said optical detector are positioned so that light interacting with said fluid passes through said window, through said optical filter, and is received by said optical detector, wherein said optical filter is structured to optically filter a plurality of predetermined orthogonal components of said light therefrom so that a characteristic of the light measured by said optical detector directly relates to the concentration of water within said fluid;
   a light source sealed in said housing so as to emit light through said window to interact with said fluid; and
   a processing and telemetry module operably coupled to said optical detector and arranged to determine an amount of water ingress into said fluid from said characteristic of said predetermined orthogonal components of said light, and to telemeter the amount of water ingress to a remote location;
   wherein said housing is threaded such that the housing is arranged to be threaded into a socket from an outer end of said housing.

2. The sensor of claim 1 wherein: said fluid includes a lubricant.

3. The sensor of claim 2 wherein: said fluid includes a grease.

4. The sensor of claim 1 wherein: said housing is fluid-tight.

5. The sensor of claim 1 wherein: said optical filter includes an integrated computational element.

6. A drill bit comprising:
   a bit body defining a socket extending to an exterior of said bit body;
   at least one cutter assembly rotatively coupled to said bit body by a bearing assembly;
   a reservoir formed in said bit body in fluid communication with said bearing assembly and said socket; and
   an optical sensor threaded into said socket in said bit body such that a window defined at an inner end of said optical sensor is in fluid communication with said reservoir, said optical sensor arranged to emit and receive light through said window for optically determining a concentration of water within a lubricant in said reservoir, and to telemeter the concentration of water to a remote location in real time.

7. The drill bit of claim 6 wherein: the optical sensor includes a light source, an optical detector, and an optical filter optically coupled to said lubricant.

8. The drill bit of claim 7 wherein: the window fluidly isolates said light source, optical detector, and optical filter from said lubricant.

9. The sensor of claim 7 wherein: said optical filter includes an integrated computational element.

10. The drill bit of claim 6 wherein: said drill bit is a roller cone bit characterized by a plurality of arms, each arm rotatively carrying a cutter assembly; and said drill bit further includes an optical sensor positioned in at least one of said plurality of arms.

11. The drill bit of claim 10 wherein: said drill bit further includes an optical sensor removably positioned in each of said plurality of arms.

12. A method of determining drill bit seal effectiveness comprising:
   providing a drill bit having a bit body, at least one cutter assembly rotatively coupled to said bit body by a sealed bearing assembly, and a reservoir formed in said bit body in fluid communication with said bearing assembly;
   disposing lubricant in said reservoir;
   threading a sensor housing into a socket defined on an exterior of said bit body;

shining light through a window at an inner end of said sensor housing to interact with lubricant at an interface of the window and the lubricant;

receiving said light reflected at said interface through said window;

selectively filtering said light received through said window;

measuring said light to determine a concentration of water within said lubricant;

telemetering the concentration of water to a remote location; and determining an effectiveness of said drill bit seal based on the concentration of water.

13. The method of claim 12 further comprising: telemetering data relating to said concentration from said drill bit to a remote location.

14. The method of claim 12 wherein said step of selectively filtering comprises: filtering a plurality of predetermined orthogonal components from said light so that a characteristic of the measured light directly relates to the concentration of said contaminant within said lubricant.

15. The method of claim 14 wherein: said step of selectively filtering is accomplished at least in part by an integrated computational element.

16. The method of claim 14 wherein said step of selectively filtering comprises: filtering a plurality of predetermined orthogonal components from said light so that a characteristic of the measured light directly relates to the concentration of water within said lubricant.

* * * * *